United States Patent
Pekonen

(10) Patent No.: US 9,861,318 B2
(45) Date of Patent: Jan. 9, 2018

(54) OPTICAL DETECTION OF MOTION EFFECTS

(71) Applicant: POLAR ELECTRO OY, Kempele (FI)

(72) Inventor: Elias Pekonen, Oulu (FI)

(73) Assignee: POLAR ELECTRO OY, Kempele (FI)

( * ) Notice: Subject to any disclaimer, the term of this patent is extended or adjusted under 35 U.S.C. 154(b) by 433 days.

(21) Appl. No.: 14/382,682

(22) PCT Filed: Feb. 25, 2013

(86) PCT No.: PCT/FI2013/050208
§ 371 (c)(1),
(2) Date: Sep. 3, 2014

(87) PCT Pub. No.: WO2013/132147
PCT Pub. Date: Sep. 12, 2013

(65) Prior Publication Data
US 2015/0038853 A1 Feb. 5, 2015

(30) Foreign Application Priority Data

Mar. 5, 2012 (FI) ...................................... 20125236

(51) Int. Cl.
*A61B 5/00* (2006.01)
*A61B 5/024* (2006.01)
(Continued)

(52) U.S. Cl.
CPC ............ *A61B 5/721* (2013.01); *A61B 5/0013* (2013.01); *A61B 5/02438* (2013.01);
(Continued)

(58) Field of Classification Search
CPC ..... A61B 5/721; A61B 5/6824; A61B 5/1118; A61B 5/0013; A61B 5/6823;
(Continued)

(56) References Cited

U.S. PATENT DOCUMENTS 5,795,300 A * 8/1998 Bryars ............... A61B 5/02433
600/500
6,553,251 B1 * 4/2003 Landesmaki ........ A61B 5/0006
600/519
(Continued)

FOREIGN PATENT DOCUMENTS

EP   1297784 A1   4/2003
EP   2371279 A1   10/2011
(Continued)

OTHER PUBLICATIONS

Gibbs et al., Reducing Motion Artifact in Wearable Bio-Sensors Using MEMS Accelerometers for Active Noise Cancellation, American Control Conference pp. 1581-1586 (Jun. 8-10, 2005).
(Continued)

*Primary Examiner* — Sanjay Cattungal
(74) *Attorney, Agent, or Firm* — Hoffmann & Baron, LLP

(57) ABSTRACT

There is provided a wearable item configured to be placed at least partially against a skin of a person; and an optically sensitive detector mounted to the wearable item and configured to detect optical signals reflected from the skin of the person, wherein the detected optical signals represent a relative motion between the wearable item and the skin of the person and wherein the optically sensitive detector is mounted to the wearable item such that there is a predetermined space between the optically sensitive detector and the skin of the person.

12 Claims, 4 Drawing Sheets

(51) Int. Cl.
*A61B 5/11* (2006.01)
*A61B 5/1455* (2006.01)
*A61B 5/0408* (2006.01)

(52) U.S. Cl.
CPC .......... *A61B 5/1118* (2013.01); *A61B 5/1128* (2013.01); *A61B 5/6823* (2013.01); *A61B 5/6824* (2013.01); *A61B 5/6831* (2013.01); *A61B 5/02427* (2013.01); *A61B 5/04085* (2013.01); *A61B 5/14551* (2013.01); *A61B 2562/0233* (2013.01)

(58) Field of Classification Search
CPC . A61B 5/1128; A61B 5/02438; A61B 5/6831; A61B 5/02427; A61B 5/04085; A61B 2562/0233; A61B 5/14551
USPC .................................. 600/473–480, 509–521
See application file for complete search history.

(56) References Cited

U.S. PATENT DOCUMENTS

| | | |
|---|---|---|
| 2006/0122520 A1 | 6/2006 | Banet et al. |
| 2007/0078318 A1 | 4/2007 | Kling et al. |
| 2009/0054751 A1 | 2/2009 | Babashan et al. |
| 2009/0292193 A1 | 11/2009 | Wijesiriwardana |
| 2010/0030088 A1* | 2/2010 | Carney .............. A61B 5/02427 600/500 |
| 2010/0145171 A1 | 6/2010 | Park et al. |
| 2011/0105874 A1 | 5/2011 | Feddes et al. |
| 2015/0208933 A1* | 7/2015 | Satomi ............... A61B 5/02416 600/479 |
| 2016/0007931 A1* | 1/2016 | Rubin ................ A61B 5/02438 600/484 |
| 2016/0143586 A1* | 5/2016 | Nousiainen ........ A61B 5/02416 600/508 |

FOREIGN PATENT DOCUMENTS

FR    2912049 A1    8/2008
WO    WO9613208 A1    5/1996

OTHER PUBLICATIONS

Tuomo Reiniaho, Finnish Search Report for corresponding Finnish Patent Application No. 20125236, pp. 1-2 (dated Nov. 16, 2012).
Jens Clevorn, International Search Report for corresponding PCT Application No. PCT/FI2013/050208, pp. 1-4 (dated Mar. 13, 2014).

* cited by examiner

OPTICAL DETECTION OF MOTION EFFECTS

CROSS-REFERENCE TO RELATED APPLICATIONS

This application is a National Stage application of International Application No. PCT/FI2013/050208, filed Feb. 25, 2013, which claims benefit to Finnish Application No. FI 20125236, filed Mar. 5, 2012, which are incorporated by reference herein in their entirety.

BACKGROUND

Field

The invention relates generally to detection of motion effects during an exercise activity and applying the detected motion effects in determining physiological effort.

Description of the Related Art

It is desirable for a person exercising to be aware of his/her heart pulse rate or another parameter related to physiological effort, such as energy expenditure. In order to acquire such information, it is common to measure the heart pulses with a strap or belt attached to the user's chest, wherein electrodes in the strap detect an electrocardiogram (ECG) signal of the user. As a consequence, the heart rate may be calculated from the detected heart pulse waveform. However, there are drawbacks in the known detection techniques which include complexity of wearing additional structures and/or unreliability of the results obtained, for example.

SUMMARY

Embodiments of the invention seek to improve the reliability of physiological effort determination.

According to an aspect of the invention, there are provided apparatuses as specified in claims 1 and 14.

According to an aspect of the invention, there is provided a computer program product embodied on a distribution medium readable by a computer and comprising program instructions which, when loaded into an apparatus, cause the apparatus to carry out any of the embodiments as described in the appended claims.

According to an aspect of the invention, there is provided a computer-readable distribution medium carrying the above-mentioned computer program product.

According to an aspect of the invention, there is provided an apparatus comprising means configured to cause the apparatus to perform any of the embodiments as described in the appended claims.

According to an aspect of the invention, there is provided an apparatus comprising means for performing any of the embodiments as described in the appended claims.

Embodiments of the invention are defined in the dependent claims.

BRIEF DESCRIPTION OF THE DRAWINGS

In the following, the invention will be described in greater detail with reference to the embodiments and the accompanying drawings, in which.

DETAILED DESCRIPTION

Figure 1:
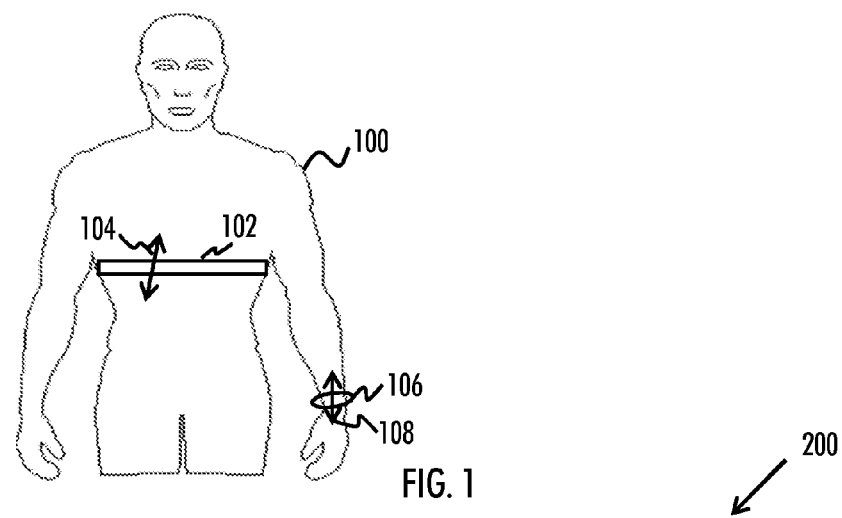
FIG. 1 presents a person wearing a chest belt and a wrist computer.

The following embodiments are exemplary. Although the specification may refer to "an", "one", or "some" embodiment(s) in several locations of the text, this does not necessarily mean that each reference is made to the same embodiment(s), or that a particular feature only applies to a single embodiment. Single features of different embodiments may also be combined to provide other embodiments.

Heart activity determination may be problematic when the person whose heart activity is to be determined is in motion. In particular, due to the motion of the person, the sensor for detecting the heart pulse may not be stable with respect to the skin of the person wearing the sensor. Looking at FIG. 1, a person 100 may be wearing an apparel, such as a chest belt or strap 102, comprising electrodes for detecting the ECG signal. As shown with an arrow 104, the chest belt 102 may move with respect to the skin of the person 100. The motion artifacts affect the reliability of the ECG detection, because the electrodes may not be stable with respect to the skin. When determining the heart rate optically from a wrist, as shown with the wrist device 106, the relative motion 108 between the wrist device 106 and the skin may cause measurement errors which arise from the fact that the optical transmission coefficient may vary as a function of motion. As the heart activity is detected by an optically sensitive detector from an optical signal, which is reflected from the human tissue and modulated by a blood pulse in the human blood circulation system, any motion artifact may decrease the reliability of the optical blood pulse detection.

The relative motion affects the heart rate measurement through various mechanisms, such as a static electricity and a change of impedance in the skin-to-electrode interface, thus generating motion artifacts into the electrocardiogram signal, for example. These motion artifacts may be arbitrary or regular. As shown with the arrows 104, 108, the apparel 102, 106 may move in any direction. Further, the apparel 102,106 may move away from the detection surface such that the distance between the skin and the apparel 102,106 may vary, for example. The arbitrary motion artifacts arise from instantaneous unexpected body movements, while regular artifacts typically arise from the human rhythmic motion, such as walking or running. The motion artifacts may fall to the same frequency range as the heart pulses, which may make it difficult for the motion artifacts to be identified from a sequence of heart pulse detections. Such problem may occur regardless of whether the heart pulse detections were obtained by the electrodes or by the optically sensitive detector. This may result in an erroneous heart pulse and/or heart activity assessment.

Therefore, it is important to provide a solution for improving the reliability of determining a physiological effort measure for physical activity. Accordingly, referring to FIGS. 2A and 2B, an apparatus 200 is provided, wherein the apparatus 200 comprises a wearable item 202 configured to be placed at least partially against a skin 210 of a person 100 during an exercise, for example. An example of a wearable item 202 is the heart rate chest belt/strap 102 of FIG. 1. FIG. 2A represents a front view of the apparatus 200 whereas FIG. 2B represent a side view of the apparatus 200 placed against the skin 210 of the person 100. In the example embodiment, where the wearable item 202 is the chest strap, it may be understood that the view of FIG. 2B is seen by the person 100 when wearing the chest belt and looking downwards to the chest belt. The vertical dashed lines in FIGS. 2 to 6 imply that the figures may show only a part of the wearable item 202.

The apparatus 200 may further comprise a processing unit 230 including at least a control circuitry (CTRL) connected to at least one memory (MEM) including a computer program code, for performing predetermined functions. The processing unit 230 may be mounted, coupled, connected, or releasably attached to the wearable item 202, for example.

The apparatus 200 further comprises an optically sensitive detector (OSD) 204 mounted to the wearable item 202 and configured to detect optical signals 206 reflected from the skin 210 of the person 200. The OSD 204 may be at least operatively connected to the processing unit 230. There may be more than of the OSDs, but for the sake of simplicity, the figures and the description focus on examples with one OSD 204. Mounting the OSD 204 to the wearable item 202 may be arranged by gluing or fastening by means of a knob, for example. The OSD 204 may be fixed to the wearable item 202. However, in an embodiment, the OSD 204 may be releasably attached to the wearable item 202, thus allowing, for example, lavation of the wearable item 202 more easily by detaching the OSD 204.

The OSD 204 is mounted to the wearable item 202 such that there is a predetermined space 208 between the OSD 204 and the skin 210 of the person 200. Thus, even though the wearable item 202 may lie against the skin 210 of the person 200, the OSD 204 may avoid direct skin contact. The space 208 may be an air space between the skin 210 and the OSD 204. It may be understood that instead of having only a detector-skin interface, the proposed solution provides two interfaces, firstly a detector-air interface and secondly an air-skin interface.

In this way the optical measurement arrangement is isolated from the skin 210 so that the blood oximetry signal does not modulate the detected optical signal. Thus, owing to the proposed arrangement, the detected optical signal carries motion information only, and in particular, the blood pulse related information is small or negligible. This may be advantageous in that the motion information may be used to determine motion artifacts. The information on the motion artifacts (e.g. the relative motion between the wearable item 202 and the skin 210) may be used to improve the reliability of the heart rate determination and/or to determine at least one physiological activity measure. If the OSD 204 was against the skin without any space 208, the detected optical signal 206 would be modulated by a blood pulse and the detected optical signal 206 would carry also information related to the blood pulse.

Figure 6:
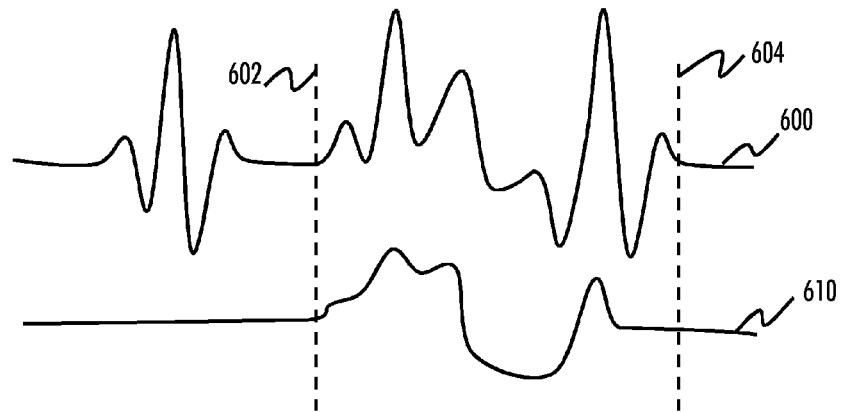
FIG. 6 shows example waveforms for the sequences of detected optical signals and of the detected heart pulses.

As shown in FIG. 2B, The OSD 204 detects reflected optical signals 206. A sequence of detected optical signals, such as the sequence 610 of FIG. 6, may be generated from adjacent detections. The sequence 610 may have a certain waveform corresponding to the detected optical signals 206. When the wearable item 202 stays substantially stable with respect to the skin 210 of the person 100, the waveform may be substantially flat. However, the waveform may comprise peaks and irregularities, as shown in FIG. 6 between vertical dashed lines 602 and 604, when the wearable item 202 experiences motion with respect to the skin 210 of the person 100. Thus, a waveform change in the sequence 610 of the detected optical signals 206 may represent a relative motion between the wearable item 202 and the skin 210 of the person 100.

In an embodiment, the space between the OSD 204 and the skin is acquired such that the wearable item 202 comprises a recess 212 for mounting the optically sensitive detector 204 and for arranging the predetermined space 208 between the OSD 204 and the skin 210 of the person 100. The recess 212 may be molded or cut to the wearable item 202 so that when the OSD 204 is placed against the backend of the recess 212, there is a space 208 between the OSD 204 and the skin 210. The space 208 may have predetermined dimensions, the knowledge of which may be acquired by empirical testing, for example. Appropriate depth may be, for example, few millimeters. The predetermined depth and width dimensions may ensure that the optical signals need to travel through the air medium. This may ensure that the blood pulses below the skin do not modulate the optical signal.

In an embodiment, the recess 212 may have straight angles, as shown in Figures. However, in another embodiment, the recess 212 may instead be semicircular, for example. That is, the form of the recess 212 is not limited as long as it provides the space 208. In an embodiment, the surface material of the recess 212 may be the same as the wearable item 202. In another embodiment, the surface of the recess 212 is covered with light reflecting material. In an embodiment, the surface of the recess 212 may be light non-transparent, i.e. it does not allow optical light to penetrate.

Alternatively in an embodiment, although not shown, the optically sensitive detector 204 may be embedded inside the wearable item 202 and the wearable item may be made of optically transparent material at least for the part between the OSD 204 and the skin 210. This may also ensure that the blood pulses below the skin do not modulate the optical signal and, consequently, that the detected optical signal 206 carries only motion artifact related information.

In an embodiment, as shown in FIG. 2, the OSD 204 itself radiates optical radiation signals and detects the transmitted optical signals 206 after they are reflected from the skin 210. Thus, in this case, no separate optical radiation source is needed.

Figure 3A:
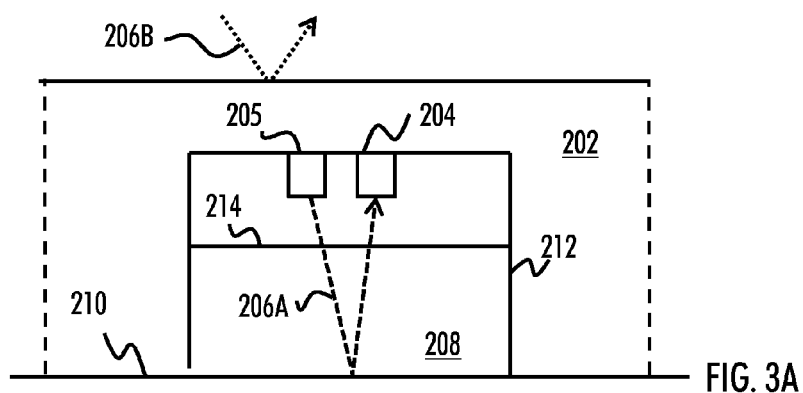

However in an embodiment as shown in FIG. 3A, the apparatus further comprises an optical radiation source (ORS) 205 mounted to the wearable item 202 and configured to provide optical radiation 206A such that the optically sensitive detector 204 is able to detect the optical radiation 206A reflected from the skin 210 of the person 100. There may be more than one optical radiation source 205 although the FIG. 3A illustrates only one for the sake of simplicity.

In an embodiment, the source 205 of the optical radiation 206A is a light emitting diode (LED). The LED may provide light with a predetermined wavelength. It may be advantageous to apply a certain wavelength which provides adequate reflection properties, for example. The ORS 205 may likewise be mounted in the recess 212 or embedded in the wearable item 202. The ORS 205 may provide optical radiation with constant intensity so that each change in the detected signal is due to motion effect and not due to changed power of optical radiation.

As the OSD 204 detects the optical radiation 206A reflected from the skin 210, the wearable item 202 may, in an embodiment, be at least partially optically non-transparent in order to prevent any ambient light 206B to be detected by the OSD 204. Thus, ambient light 206B may bounce back from the wearable item 202, as shown in FIG. 3A. In an embodiment, the optically non-transparent requirement is fulfilled only for the part of the wearable item 202 where any ambient light would otherwise be detected by the OSD 204. This may be advantageous so that the OSD 204 does not detect any other optical radiation signals except the radiation from the ORS 205. Thus, the reliability of the optical signal 206 detection may be improved.

In an embodiment, the apparatus 200 further comprises a lens 214 placed in front of the optical radiation source 205. In an embodiment, the lens 214 is transparent only to optical radiation 206A of the optical radiation source 205. This may be optical radiation 206A having a predetermined wavelength. Therefore, the wavelength of the optical radiation 206A may be adjusted by changing the lens 214. Thus, the radiation source 205 need not be changed.

In an embodiment, the same lens 214 or an additional lens (not shown) may be placed also in front of the ODS 204. This may increase the reliability of detecting only radiation having a certain wavelength. Such a lens 214 may additionally protect the ORS 205 and/or the OSD 204 from damages and dirt.

Figure 3B:
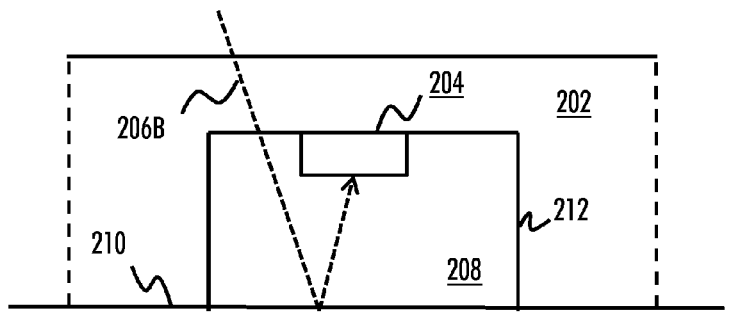

In an embodiment, the source of the optical radiation is ambient light 206B, as shown in FIG. 3B. The wearable item 202 is at least partially optically transparent in order to allow ambient light 206B to penetrate the wearable item 202 and to be reflected from the skin 210 of the person 100 to the optically sensitive detector 204. In an embodiment, the optically transparent requirement is fulfilled only for the part of the wearable item 202 so that ambient light 206B may be detected by the OSD 204 only after reflection from the skin 210. This embodiment may allow for reducing the battery consumption of the apparatus 200 as no battery power is then needed for the optical radiation source 205.

In an embodiment, the motion effects can be used in determining physiological effort, such as running speed or physical activity. In one embodiment, the apparatus 200 and, in particular, the processing unit 230 together with the memory may cause the apparatus 200 to transmit an indication of the detected optical signals 206 to a separate processing unit, such as a wrist watch or a personal exercise computer unit, manufactured by Polar Electro, for example. The separate processing unit may then determine at least one physiological activity measure representing the activity of the person 100 based on the sequence 610 of the detected optical signals 206.

The sequence 610 of FIG. 6 may be characterized by a certain waveform. The time structure of the optical signal waveform comprises a contribution from the motion intensity of the person 100 (i.e. the user). Thus, when there has been motion between the skin 210 and the wearable item 202, it may be determined that the person 100 has performed some activity. The larger the variation in the waveform of the sequence 610 is, the higher may be the amount activity performed, for example. Thus, the physiological effort or activity measure may be obtained by examining the time structure of the optical signal sequence waveform. This activity may be converted into a physiological activity measure, which may characterize the physiological output of the person 100.

In an embodiment, the physiological activity measure is a cadence of running or walking motion. This may be determined by analyzing the frequency of peaks in the waveform of the sequence 610.

In an embodiment, the physiological activity measure is a peak or average speed of running or walking motion.

In an embodiment, the physiological activity measure is a frequency of performing activities.

In an embodiment, the physiological activity measure is energy expenditure. There may be, for example, empirical testing performed which may have indicated the amount of energy consumption for a certain type of waveform of the sequence 610.

In an embodiment, the physiological activity measure is a type of sport performed. As an example, swimming may provide different waveform of the sequence 610 than running or walking. Consequently, the type of sport may be identified based on the sequence 610 of the detected optical signals 206. As different sports vary in a metabolic equivalent of task (MET)-values, the activity performed indicates intensity of the physiological effort, for example.

In an embodiment, the physiological activity measure is a time duration, which is spent for performing activities. In an embodiment, the time may accumulate only when the waveform of the sequence 610 exceeds a certain threshold. The threshold may refer to a certain level of variation, or to a certain min-max ratio of the waveform.

In an embodiment, the processing unit 230 together with the memory may cause the apparatus 200 itself to determine the at least one physiological activity measure representing the activity of the person 100 based on the sequence of the detected optical signals 206. Further, in an embodiment, the apparatus 200 may comprise a display and a user interface to show and browse through information shown on the display. In this case, the information shown on the display may comprise information about the determined physiological activity measure. Thus, the apparatus 200 need not transmit any indications to a separate processing unit, but the apparatus 200 may perform the computational functionalities by itself. This embodiment may be possible, for example, when the apparatus 200 is comprised in a wrist watch or a personal exercise computer unit, manufactured by Polar. The components, such as the OSD 204 may be on the back side of the wrist watch, for example. The backside of the wrist watch may also be equipped with a recess for accommodating the OSD 204 and the ORS 205, if needed.

The physiological activity measure may be shown to the person 100 in real time during his/her exercise. Alternatively or in addition to, the activity measure(s) may be determined on the background during the exercise and shown to the person 100 on request, possibly at a later time after the exercise.

Figure 4:
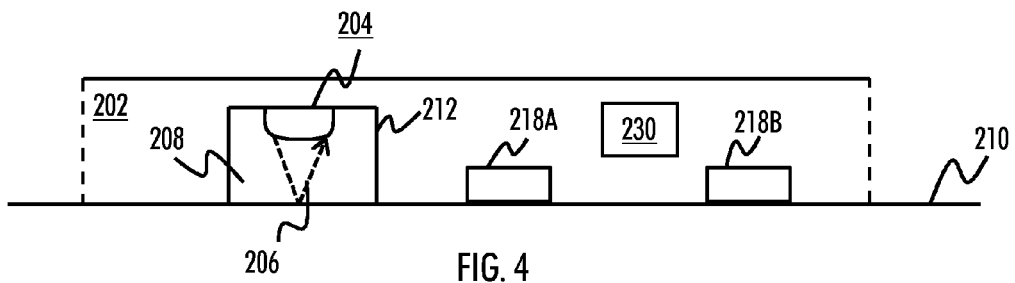

Referring to FIG. 4, in an embodiment, the apparatus further comprises at least one sensor 218A, 218B, 220 mounted to the wearable item 202 and configured to detect heart activity of the person 100. In an embodiment, the heart activity comprises pulses of the person 100. The at least one sensor 218A, 218B, 220 is mounted to the wearable item 202 so that the detected optical signals 206 represents a relative motion between the at least one sensor 218A, 218B, 220 and the skin 210 of the person 100. This may be enabled by mounting the OSD 204 and the at least one sensor 218A, 218B, 220 close to each other in the wearable item 202 so that the detected motion artifact by the OSD 204 characterizes also the motion artifact experienced by the at least one sensor 218A, 218B, 220. The physical separation between a sensor 218A, 218B, 220 and the OSD 204 may be between 0 millimeter and 10 millimeters, for example. The 0 millimeter case may take place when the sensor, such as an electrode, comprises a portion for mounting the OSD 204 within the sensor. The surface of the sensor may, for example, comprise a hole, a slot, or an empty space (e.g. free of the sensor surface material) for mounting the OSD 204. Thus, the recess 212 for mounting the OSD 204 may be formed within the region of the electrode, e.g. inside an area defined by the edges of the electrode.

In an embodiment, the at least one sensor comprises at least two electrodes 218A, 218B, as shown in FIG. 4, configured to detect an electrocardiogram (ECG) signal of the person 100. Thus, the overall measurement configuration comprises two electrodes 218A, 218B for measuring electric heart activity signal and an optical measurement head 204 for the motion artifact measurement. In this case, the wearable item 202 may be located against the chest or other places of human body, where the ECG signal may be detected. In an embodiment, the electrodes 218A, 218B are relatively close to each other so that the optical motion artifact signal detected by the OSD 204 represents also the motion of both electrodes 218A, 218B. In an embodiment, the OSD 204 may be located, for example, between the two detectors 218A, 218B. In an embodiment, there are two OSDs 204 mounted to the wearable item 202. It may be that one of them is mounted within one electrode 218A and the other OSD is mounted within the second electrode 218B. Thus, each of the detectors 218A, 218B may comprise a recess for mounting an OSD 204, and possibly also for mounting a radiation source for the OSD, if needed. This may allow for an accurate representation of the motion of the detectors 218A, 218B.

The electrodes 218A, 218B detect the electric volts generated for each heart beat and thus provide information to generate a sequence of detected heart pulses. An example of such sequence is shown in FIG. 6 with reference numeral 600, for example. The waveform of the sequence 600 may correspond to the detected heart pulse related signals. The sequence 600 may be generated from adjacent heart pulse detections.

Figure 5:
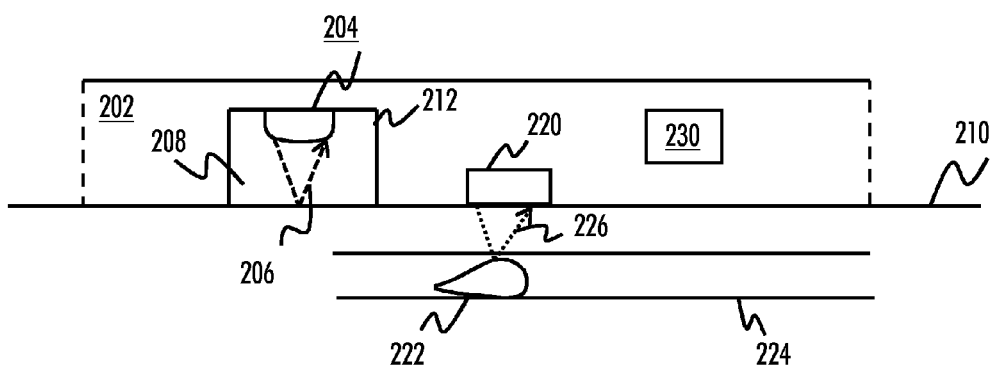

In another embodiment, as shown in FIG. 5, an optical heart rate measurement may be applied. In this embodiment, the at least one sensor comprises a second optically sensitive detector 220 configured to detect blood pulses 222 optically from the blood circulation 224 of the person 100. Thus, the overall measurement configuration in this embodiment comprises a first optical measurement head 204 for the motion artifact measurement and a second optical measurement head 220 optical blood oximetry-based heart activity measurement. In this case, the apparatus 200 may be located in any location of the human body where skin 210 surface is available. Suitable locations comprise, for example, a chest, a leg, an arm, a wrist, an ear and a finger. The second OSD 220 may detect the heart pulses and thus the sequence 610 of detected heart pulses may be formed. The apparatus 200 may also comprise another radiation source for providing optical radiation 226 usable by the second OSD 220. Alternatively, the OSD 220 may transmit the optical radiation 226 itself.

Let us discuss the human blood circulation in more detail. As the heart muscle of a person 100 contracts, oxygenated blood is pumped to the cardiovascular system, which results in a blood pressure alteration in the blood circulation. The oxygenated blood is pumped through the arterial circulation system to human cells. The blood is deoxygenated in the human cells and returned back to the heart via a venous circulatory system. As the blood circulates in the arterials and in the veins, the blood pressure pulses can be observed from both of them. Moreover, the human blood circulation is a closed system, meaning that exactly the same amount of blood is pumped from the heart as is received by the heart. This enables the same modulation of blood pulses to be observed from the veins as from the arteries. Thus, the blood circulation 224 depicted in FIG. 5 may refer to an artery or to a vein. Further, blood travels also in a person's microcirculation system (also known as a microvascular blood flow or a microvascular system) and, therefore, the blood pressure pulse 222 can be detected from the microcirculation of the skin 210, as well.

However, as the at least one sensor, such as the electrodes 218A and 218B or the second OSD 220, is mounted to the wearable item 202, the at least one sensor may also experience motion with respect to the skin 210. The motion may cause the waveform of the sequence 600 to have irregularities as shown in FIG. 6 between the two dashed vertical lines 602 and 604. Therefore, it may be troublesome to determine the person's heart rate as the sequence 600 may comprise motion artifacts.

In an embodiment, the processing unit 230 may apply the sequence 610 of detected optical signals 206 to the sequence 600 of the detected heart pulses in order to reduce motion artifacts from the sequence 600 of the detected heart pulses. Looking at FIG. 6, for example subtracting the sequence 610 from the sequence 600 may result in a waveform which characterizes the heart pulse detections without motion artifacts. Heart pulses may be used for characterizing a user's cardiovascular activity. Further, heart pulses may be applied for calculating a heart rate, i.e. the frequency of heart beats, heart beat intervals, and/or heart rate variability. Thus, the reliability for characterizing a user's cardiovascular activity may be improved.

In an embodiment, the processing unit 230 may decide to transmit an indication of the detected optical signals 206 and of the detected heart pulses to a separate processing unit, such as a wrist watch or a personal exercise computer unit, for example, in order to allow the separate processing unit to apply the sequence 610 of detected optical signals to the sequence 600 of the detected heart pulses in order to reduce motion artifacts from the sequence 600 of the detected heart pulses. The separate processing unit may obtain the sequence waveforms 600 and 610 based on the indications of detections of the apparatus 200. Alternatively, the processing unit 230 may generate such sequence waveforms 600 and 610 and transmit and indication of the sequence waveforms 600 and 610 to the separate processing unit.

In both embodiments of FIGS. 4 and 5 there may be several ways to eliminate or to reduce the motion artifact component from the heart activity signal sequence 600. In an embodiment the subtraction or deduction between the two sequences 600, 610 is performed as a time domain process. Thus, the sequence waveform 610 is subtracted from the sequence waveform 600 in time domain.

In another embodiment, the sequence 610 is applied to the sequence 600 in frequency domain. This may require a Fourier transform to be performed for both of the sequences 600 and 610 before separating the motion artifacts from the sequence waveform 600. This embodiment may be advantageous in that the frequency domain process may discard the directions of the experienced motion.

In an embodiment, the lengths of the sequence 600 of the detected heart pulses and the sequence 610 of the detected optical signals 206 are the same. In other words, the number of samples in the two sequences is the same. This may further simplify the process of separating the motion artifacts from the sequence waveform 600.

Figure 2A:
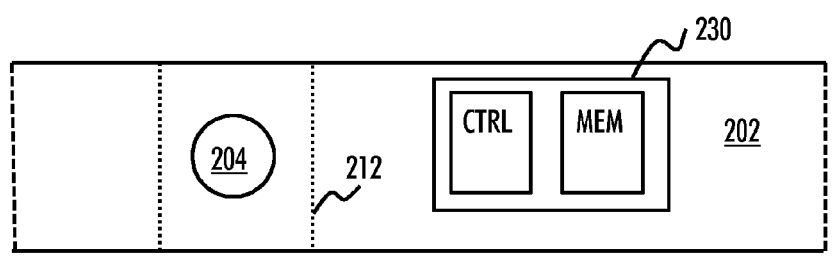
FIGS. 2A, 2B, 3A, 3B, 4, and 5 show apparatuses according to some embodiments.
Figure 2B:
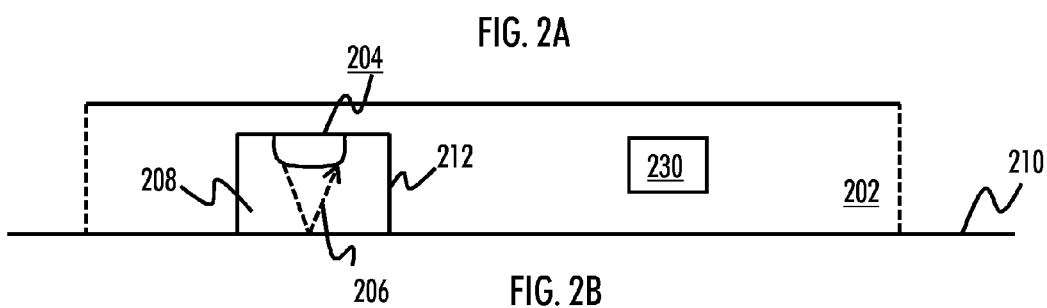

In an embodiment, the wearable item is a heart rate chest belt, such as the one shown with reference numeral 102 in FIG. 1. The chest belt may accommodate the OSD 204, a processing unit 230 and possibly some other sensors, such as the electrodes 218A, 218B for detecting the ECG signal of the person 100. The advantages in the measurement from the chest area may be that at least part of electronics and mechanics may be shared between the ECG-based heart rate measurement and the optical measurement and further that the chest area is close to the center or mass of the person 100, thus characterizing the user's overall motion accurately.

In an embodiment, the wearable item is a wrist band, such as a band of the wrist device 106 shown in FIG. 1. The components, such as the OSD 204 and possibly the second OSD 220 may be mounted on the inner surface of the band, for example.

In an embodiment, the wearable item is a wrist computer. In this case, the components may be mounted to the backside of the wrist watch. This embodiment may allow for applying the controller circuitry/ies of the wrist watch. Thus, there may not be any need for wireless transfer of information regarding the optical signal 206 detections or the heart pulse detections. In an embodiment, the wearable item is an ear unit comprising an attachment structure, such as a clip, for attaching the ear unit to the user's ear.

Figure 7:
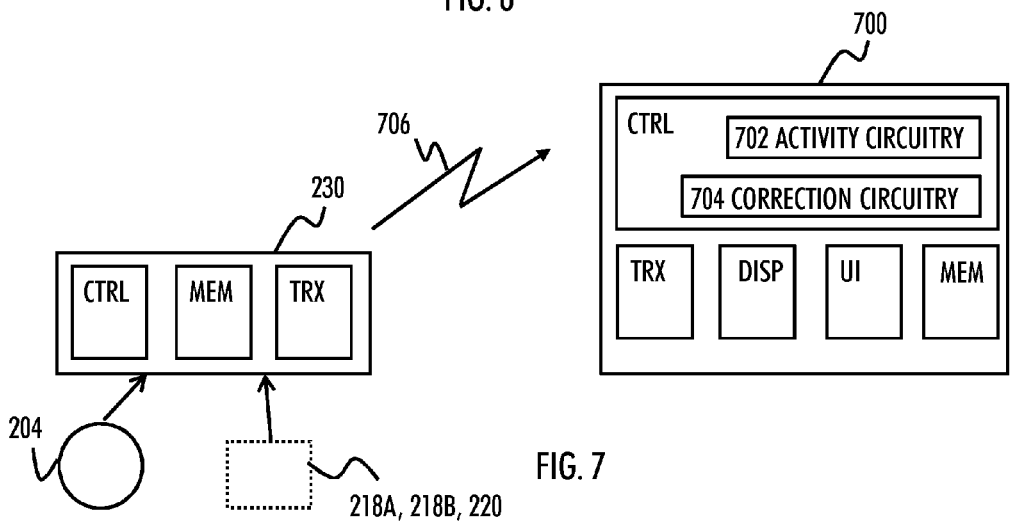
FIGS. 7 and 8 illustrate processing units according to some embodiments.
Figure 8:
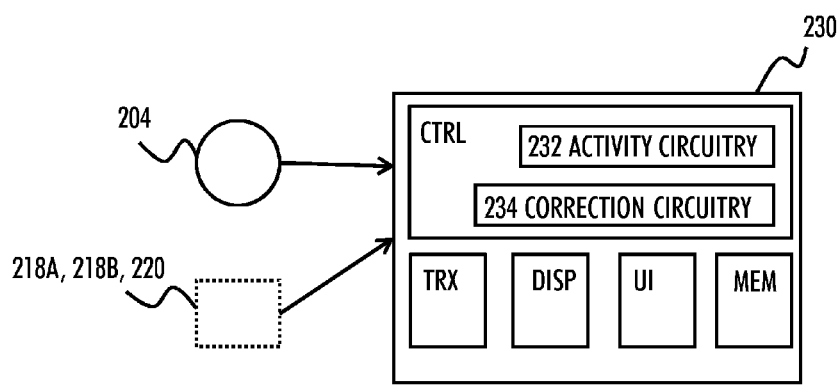

FIGS. 7 and 8 show two embodiments of a processing unit 230 comprised in the apparatus 200. FIG. 7 also shows a separate processing unit 700. It should be noted that FIGS. 7 and 8 show only the elements and functional entities required for understanding embodiments. Other components have been omitted for reasons of simplicity. It is apparent to a person skilled in the art that the processing units 230 and 700 may also comprise other functions and structures. Although not shown, each of the apparatuses in FIGS. 7 and 8 may comprise one or more batteries.

Looking at FIG. 7, an example wearable item 202, where the processing unit (or a processor) 230 may be mounted, is a chest belt. The separate processing unit (or a processor) 700 may be mounted in a wrist computer, for example. The processing units 230 and 700 may each comprise a control circuitry (CTRL), e.g. a chip, a processor, a micro controller, or a combination of such circuitries causing the processing unit 230, 700 to perform predetermined functionalities. The control circuitries (CTRL) may be implemented with a separate digital signal processor provided with suitable software embedded on a computer readable medium, or with a separate logic circuit, such as an application specific integrated circuit (ASIC). The control circuitries (CTRL) may comprise an interface, such as computer port, for providing communication capabilities. The memories (MEM) may store software executable by the at least one control circuitry (CTRL). The memories (MEM) may be implemented using any suitable data storage technology, such as semiconductor based memory devices, flash memory, magnetic memory devices and systems, optical memory devices and systems, fixed memory and removable memory. The memories (MEM) may be for storing data related to detections of optical signals 206 and possibly to the detections of heart pulses, for example.

In FIGS. 7 and 8 the processing unit 230 is at least operatively connected to the OSD 204 and to the at least one heart pulse sensor 218A, 218B, 220 for receiving information related to the detections.

The processing units 230 and 700 may each further comprise radio interface components (TRX) providing radio communication capabilities with the radio access air interface. The TRX of the processing unit 230 may transmit information 706 regarding the detections of the blood pulses and/or of the optical signals 206 wirelessly during operation to the TRX of the processing unit 700. The information 706 may be transmitted in a radio frequency signal. Further, for example, the radio frequency transmission may utilize the Bluetooth® standard, or any other suitable standard/non-standard wireless communication methods utilizing electric and/or magnetic fields. An exemplary frequency for this type of transmission is 2.4 GHz, for instance. Alternatively, the transmission may be performed via magnetic pulses that are transmitted through coils in the TRXs. An exemplary frequency for this type of transmission is 5.5 kHz.

The separate processing unit 700 comprised in a wrist computer, in a palm computer or in a mobile phone, for example, may further comprise a display (DISP) and a user interface (UI) for accessing the information shown in the display and for changing settings of the processing unit 700. The display may be a liquid crystal display (LCD) and the UI may comprise various elements, such as keys, buttons, a microphone, a touch display, etc.

In an embodiment, the control circuitry (CTRL) of the separate processing unit 700 may comprise an activity circuitry 702 for determining the at least one physiological activity measure based on the indications of the sequence 610 of the detected optical pulses 206.

In an embodiment, the control circuitry (CTRL) of the separate processing unit 700 may comprise a correction circuitry 704 for improving the reliability of the heart rate determination. The processing unit 700 may have obtained the indication 706 of the detected heart pulses and of the detected optical signals 206 from the apparatus 200. Based on the indications 706, the correction circuitry 704 may apply the sequence 610 of the optical signals 206 to the sequence of the heart pulses 600 in order to reduce motion artifacts from the sequence 600 of the heart pulses. Therefore, the determination of the heart rate or the heart rate variation may be performed without the motion artifacts causing errors in the waveform of the sequence 600 of the detected heart pulses.

FIG. 8 on the other hand provides an embodiment where the wearable item 202 mounts a processing unit 230 capable of performing the computational functionalities itself. The processing unit 230 may comprise a display (DISP) and a user interface (UI) for accessing the information shown in the display and for changing settings of the processing unit 230. The display may be a liquid crystal display (LCD) and the UI may comprise various elements, such as keys, buttons, a microphone, a touch display, etc. The processing unit 230 need not necessarily send any indications 706 to a separate processing unit 700.

In an embodiment, the control circuitry (CTRL) of the processing unit 230 may comprise an activity circuitry 232 for determining the at least one physiological activity measure.

In an embodiment, the control circuitry (CTRL) of the processing unit 230 may comprise a correction circuitry 234 for improving the reliability of the heart rate determination. The correction circuitry 234 may apply the sequence 610 of the optical signals to the sequence 600 of the heart pulses in order to reduce motion artifacts from the sequence 600 of the heart pulses.

As used in this application, the term 'circuitry' refers to all of the following: (a) hardware-only circuit implementations, such as implementations in only analog and/or digital circuitry, and (b) combinations of circuits and software (and/or firmware), such as (as applicable): (i) a combination of processor(s) or (ii) portions of processor(s)/software including digital signal processor(s), software, and memory(ies) that work together to cause an apparatus to perform various functions, and (c) circuits, such as a microprocessor(s) or a portion of a microprocessor(s), that require software or firmware for operation, even if the software or firmware is not physically present. This definition of 'circuitry' applies to all uses of this term in this application. As a further example, as used in this application, the term 'circuitry' would also cover an implementation of merely a processor (or multiple processors) or a portion of a processor and its (or their) accompanying software and/or firmware. The term 'circuitry' would also cover, for example and if applicable to the particular element, a baseband integrated circuit or applications processor integrated circuit for a mobile phone or a similar integrated circuit in a server, a cellular network device, or another network device.

Figure 9:
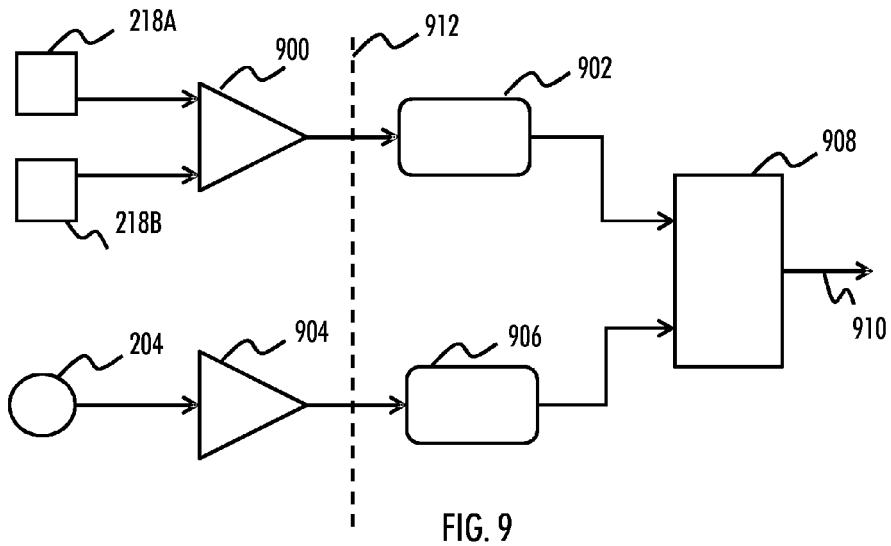
FIG. 9 presents a signal processing block diagram according to an embodiment.

FIG. 9 provides an example block diagram of a signal processing arrangement for improving the reliability of heart rate determination. The arrangement may include at least one heart pulse sensor 218A, 218B. Alternatively, the optical sensor 220 would be sufficient as well. The detections from the sensors 218A, 218B enter an amplifier 900 which combines and amplifies the detections by the sensors 218A, 218B. Next an ECG detector 902 generates the sequence 600 having a certain waveform. On the lower part of the figure, the OSD 204 detects the optical signals 206 reflected from the skin 210 of the person 100. An amplifier 904 may amplify the detections in order to allow a motion artifact detector 906 to form the sequence 610 of the optical signal detections. The sequences are forwarded to a combination circuitry 908 which combines the two sequences 600 and 610 so that the motion artifacts included in the heart pulse sequence 600 are reduced or eliminated. As a result, the output 910 is a heart pulse detection sequence waveform without motion artifacts. The dashed vertical line 912 illustrates that the part of the Figure on the left of the dashed vertical line 912 may be performed in the apparatus 200, whereas the part of the Figure on the right of the dashed vertical line 912 may be performed in another, separate processing unit 700, such as in a wrist computer or a mobile phone. Alternatively, each element of the FIG. 9 may be in the same apparatus 200.

The techniques and methods described herein may be implemented by various means. For example, these techniques may be implemented in hardware (one or more devices), firmware (one or more devices), software (one or more modules), or combinations thereof. For a hardware implementation, the apparatus(es) of embodiments may be implemented within one or more application-specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, other electronic units designed to perform the functions described herein, or a combination thereof. For firmware or software, the implementation can be carried out through modules of at least one chip set (e.g. procedures, functions, and so on) that perform the functions described herein. The software codes may be stored in a memory unit and executed by processors. The memory unit may be implemented within the processor or externally to the processor. In the latter case, it can be communicatively coupled to the processor via various means, as is known in the art. Additionally, the components of the systems described herein may be rearranged and/or complemented by additional components in order to facilitate the achievements of the various aspects, etc., described with regard thereto, and they are not limited to the precise configurations set forth in the given figures, as will be appreciated by one skilled in the art.

Thus, according to an embodiment, the apparatus comprises means configured to cause the apparatus to carry out embodiments of any of the FIGS. 1 to 10. The means may include means for detecting the optical signals, means for detecting the ECG signals, means for detecting the heart pulses optically, means for providing optical radiation, means for affecting the wavelength of the optical radiation, processing means for determining the physiological activity measure(s), means for generating the sequences from the detected optical signals and/or detected heart pulses, processing means for applying the sequence of the optical signal detections to the sequence of the heart pulse detections, etc.

Figure 10:
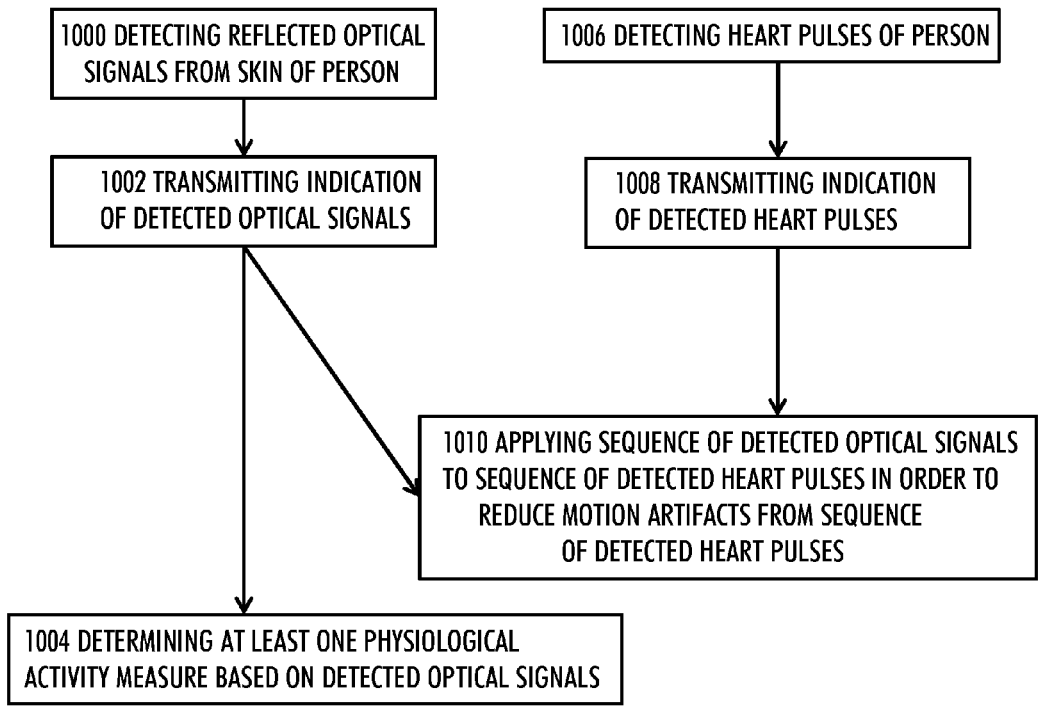
FIG. 10 depicts a method according to an embodiment.

FIG. 10 shows a method according to an embodiment. In step 1000, the method comprises detecting reflected optical signals. The detection may be made by an optically sensitive detector. In step 1002, an indication or indications of the detected optical signals is transmitted to a separate processing unit and the separate processing unit may in step 1004 determine at least one physiological activity measure based on the detected optical signals. In case no separate processing unit is needed, the step 1002 may be omitted.

In an embodiment, the method of FIG. 10 also comprises, in step 1006, detecting heart pulses of the person. In step 1008, the apparatus detecting the heart pulses may transmit an indication of the detected heart pulses to a separate processing unit, if needed. If such separate processing unit is not needed, i.e. the apparatus detecting the heart pulses may itself perform the computational functionalities and possibly also show the results to the person, step 1008 may be omitted. In step 1010, the method comprises applying a sequence of the detected optical signals to a sequence of the detected heart pulses in order to reduce motion artifacts from the sequence of the detected heart pulses.

Embodiments as described may also be carried out in the form of a computer process defined by a computer program. The computer program may be in source code form, object code form, or in some intermediate form, and it may be stored in some sort of carrier, which may be any entity or device capable of carrying the program. For example, the computer program may be stored on a computer program distribution medium readable by a computer or a processor. The computer program medium may be, for example but not limited to, a record medium, computer memory, read-only memory, electrical carrier signal, telecommunications signal, and software distribution package, for example.

Even though the invention has been described above with reference to an example according to the accompanying drawings, it is clear that the invention is not restricted thereto but can be modified in several ways within the scope of the appended claims. Therefore, all words and expressions should be interpreted broadly and they are intended to illustrate, not to restrict, the embodiment. It will be obvious to a person skilled in the art that, as technology advances, the inventive concept can be implemented in various ways. Further, it is clear to a person skilled in the art that the described embodiments may, but are not required to, be combined with other embodiments in various ways.

What is claimed is:

1. An apparatus, the apparatus comprising:
a wearable item configured to be placed at least partially against a skin of a person;
an optically sensitive detector mounted to the wearable item and configured to detect optical signals reflected from the skin of the person, wherein the optical signals represent a relative motion between the wearable item and the skin of the person and wherein the optically sensitive detector is mounted to the wearable item such that there is a predetermined non-zero space between the optically sensitive detector and the skin of the person when the wearable item is placed at least partially against the skin of the person that ensures blood pulses of the person do not modulate the optical signals and that the optical signals carry only motion artifact information; and at least one sensor mounted to the wearable item and configured to detect heart activity of the person, wherein the at least one sensor is mounted to the wearable item relative to the optically sensitive detector so that the optical signals represent a motion of the at least one sensor relative to the skin of the person.

2. The apparatus of claim 1, wherein the wearable item comprises a recess for mounting the optically sensitive detector and for providing the predetermined non-zero space between the optically sensitive detector and the skin of the person.

3. The apparatus of claim 1, further comprising:
an optical radiation source mounted to the wearable item and configured to provide optical radiation such that the optically sensitive detector is able to detect the optical signals of the optical radiation reflected from the skin of the person.

4. The apparatus of claim 3, further comprising:
a lens placed in front of the optical radiation source, wherein the lens is transparent only to optical radiation of the optical radiation source.

5. The apparatus of claim 1, wherein the wearable item is at least partially optically transparent in order to allow ambient light to penetrate the wearable item and to be reflected from the skin of the person to the optically sensitive detector.

6. The apparatus of claim 1, further comprising:
at least one processor and at least one memory including a computer program code, wherein the at least one memory and the computer program code are configured to, with the at least one processor, cause the apparatus either:
to decide to transmit an indication of the detected optical signals to a separate processing unit in order to allow the separate processing unit to determine at least one physiological activity measure representing the activity of the person based on a sequence of the detected optical signals, or to determine at least one physiological activity measure representing the activity of the person based on a sequence of the detected optical signals.

7. The apparatus of claim 1, wherein the at least one sensor comprises at least two electrodes configured to detect an electrocardiogram signal of the person.

8. The apparatus of claim 1, wherein the at least one sensor comprises a second optically sensitive detector configured to detect blood pulses optically from the blood circulation system of the person.

9. The apparatus of claim 1, further comprising:
at least one processor and at least one memory including a computer program code, wherein the at least one memory and the computer program code are configured to, with the at least one processor, cause the apparatus either:
to decide to transmit an indication of the detected optical signals and of the detected heart pulses to a separate processing unit in order to allow the separate processing unit to apply a sequence of detected optical signals to a sequence of the detected heart pulses in order to reduce motion artifacts from the sequence of the detected heart pulses, or to apply a sequence of detected optical signals to a sequence of the detected heart pulses in order to reduce motion artifacts from the sequence of the detected heart pulses.

10. The apparatus of claim 9, wherein the lengths of the sequence of the detected heart pulses and the sequence of the detected optical signals are the same.

11. The apparatus of claim 1, wherein the sequence of the detected optical signals is applied to the sequence of the detected heart pulses in a frequency domain.

12. The apparatus of claim 1, wherein the wearable item is a heart rate chest belt, a wrist band, or a wrist computer.

* * * * *